United States Patent [19]

Reynolds et al.

[11] 4,335,729

[45] Jun. 22, 1982

[54] APPARATUS AND METHOD FOR SUPPRESSING RESONANCE IN AN ELECTROMANOMETRY SYSTEM

[75] Inventors: Gordon S. Reynolds, Bountiful; Robert J. Todd, Salt Lake City, both of Utah

[73] Assignee: Sorenson Research Co., Inc., Salt Lake City, Utah

[21] Appl. No.: 129,495

[22] Filed: Mar. 11, 1980

Related U.S. Application Data

[63] Continuation-in-part of Ser. No. 62,872, Aug. 1, 1979, Pat. No. 4,269,387.

[51] Int. Cl.³ .................................................. A61B 5/02
[52] U.S. Cl. ...................................... 128/674; 128/748; 73/707; 138/46; 251/122; 251/DIG. 4
[58] Field of Search .................. 128/672, 14 675, 748; 73/707, 739; 367/152, 176; 138/43, 46; 137/207; 251/122, DIG. 4

[56] References Cited

U.S. PATENT DOCUMENTS

| | | | |
|---|---|---|---|
| 3,343,560 | 9/1967 | Nankivell | 137/207 |
| 3,581,733 | 6/1971 | Grandjean | 128/673 |
| 3,610,228 | 10/1971 | Temkin | 128/748 |
| 3,665,948 | 5/1972 | Hohberger | 73/707 X |
| 3,675,891 | 7/1972 | Reynolds et al. | 128/673 X |
| 3,877,428 | 4/1975 | Seagle et al. | 128/214 R |
| 3,896,800 | 7/1975 | Cibulka | 128/204.26 |

OTHER PUBLICATIONS

Proefschrift, "The Response of Catheter Manometer Systems Used for Direct Blood Pressure Measurements", May 1966.
Latimer, R. D. et al., *Anaesthesia*, vol. 29, 1974, pp. 307-317.
Latimer, K. E., *Bibliotheca Cardiologica*, vol. 31, 1973, pp. 7-13 and 20-27.
Crul, J. F., *Acta Anaestesiologica Scandinavica*, 6 Suppl. 11, pp. 135-169.

*Primary Examiner*—Stephen C. Pellegrino
*Assistant Examiner*—John C. Hanley
*Attorney, Agent, or Firm*—H. Ross Workman; Rick D. Nydegger; Drew S. Hamilton

[57] ABSTRACT

A novel apparatus and method for suppressing unwanted resonance in an electromanometry system. The apparatus includes a compliant air cavity connected through a variable impedance device which is coupled in parallel to the liquid-filled catheter of the electromanometry system. By varying the hydraulic impedance through which the compliant air cavity is coupled to the system, precise impedance matching capability is provided over a wide range of hydraulic impedance values, thereby permitting suppression of unwanted resonance and improved frequency response of recorded waveforms in a wide variety of catheter-transducer systems.

3 Claims, 6 Drawing Figures

APPARATUS AND METHOD FOR SUPPRESSING RESONANCE IN AN ELECTROMANOMETRY SYSTEM

This application is a continuation-in-part of our copending patent application, Ser. No. 062,872, filed Aug. 1, 1979, now issued as U.S. Pat. No. 4,269,387 to Reynolds et al.

BACKGROUND

1. Field of the Invention

The present invention relates to an apparatus and method for suppressing unwanted resonance in an electromanometry system, and in particular to an apparatus and method for matching the characteristic impedance of an electromanometry system.

2. The Prior Art

By the pumping action of the heart a quantity of incompressible blood is intermittently pumped into an elastic reservoir of blood vessels. The resistance of these blood vessels causes a build-up in the arteries of a continuous mean blood pressure with a superimposed fluctuation between a maximum and a minimum pressure, known as systolic and diastolic values, respectively. The heart's pumping action results in the cyclical recurrence of these blood pressures.

Sometimes the life of a patient depends on a continuous, accurate measurement of these cyclical blood pressures. Thus, the use of electromanometry systems for monitoring and recording hemodynamic pressures has become an indispensible technique in many modern hospitals.

In order to transform hemodynamic pressures into recordable electronic waveforms, the interior of a patient's artery may be connected via a liquid-filled catheter to an electrical pressure transducer. In this way, the periodic pulsations of blood are transmitted as pressure pulses through the liquid-filled catheter to the transducer, where they are transformed into recordable waveforms. The output of the transducer may be recorded on an oscilloscope or strip chart, from which it is possible to ascertain a number of parameters, as for example heart rate, duration of systole, and systolic, diastolic and mean pressures. Each of these parameters may provide important diagnostic data about a patient's condition.

One of the problems that is frequently encountered when using an electromanometry system is the problem of resonance. Resonance describes the tendency of a catheter-transducer system to amplify pulsations that are in the region of the system's natural resonant frequency to a much greater degree than pulsations having other frequencies. Resonance in a catheter-transducer system results in a form of distortion known as "ringing" or "harmonic ringing" in the recorded waveforms. This distortion hampers the ability of the electromanometry system to provide the needed diagnostic data in an accurate and reliable form, and limits the range of frequencies over which the system can faithfully reproduce detected hemodynamic pressures.

One of the prior art techniques for damping (i.e. suppressing) unwanted resonance is the use of electrical equilisation circuitry. See, for example, Latimer, K. E., "The Electrical Equalisation of Electromonometry and Phono Cardiography Systems," *Bibliotheca Cardiologica* 31:20 (1973). Although electrical equalisation may be used to suppress resonance distortion to a desirable degree, the necessary electronic circuitry is often complex and relatively difficult and expensive to implement, particularly in existing electromanometry systems.

Other prior art attempts to suppress unwanted resonance in catheter-transducer systems have relied on series or parallel hydraulic damping techniques. See, for example, Crul, J. F., "Measurement of Arterial Pressure," *Acta Anaesthesiologica Scandinavica* 6 Suppl. 11:135 (1962); Latimer, K. E., "Extending the Frequency Spectrum of Electromanometry Systems into Audio Frequencies," *Bibliotheca Cardiologica*, 31:7 (1973); and Latimer, R. D. and Latimer, K. E., "Continuous Flushing Systems," *Anaesthesia* 29:307 (1974).

Series or parallel hydraulic damping techniques are less expensive and more simple to use than electronic equalisation techniques, and they provide acceptable resonance suppression in many applications. However, to date there has not been devised an apparatus and method for suppressing resonance in catheter-transducer systems which is inexpensive, effective and which provides a wide range of control for use with numerous different types of electromanometry systems. Such an invention is described and claimed herein.

BRIEF SUMMARY AND OBJECTS OF THE INVENTION

The present invention comprises a novel apparatus and method for suppressing unwanted resonance in an electromanometry system. The apparatus includes a compliant air cavity connected through a variable impedance device that is coupled in parallel to the liquid-filled catheter of the electromanometry system. By varying the hydraulic impedance through which the compliant air cavity is coupled to the system, the characteristic impedance of the system may be matched, resulting in suppression of unwanted resonance and improved frequency response of the recorded waveforms over a broader range of frequencies. The invention provides a wide range of control for purposes of hydraulically matching the characteristic impedance of virtually any type of electromanometry system currently in use.

It is therefore a primary object of the present invention to provide a novel apparatus and method for suppressing unwanted resonance in an electromanometry system.

Another object of the present invention is to provide precise impedance matching capability over a wide range of hydraulic impedance values in a wide variety of catheter-transducer systems.

These and other objects and features of the present invention will become more fully apparent from the following description and appended claims taken in conjunction with the accompanying drawings.

DETAILED DESCRIPTION OF THE PREFERRED EMBODIMENTS

Reference is now made to the Figures wherein like parts are designated with like numerals throughout.

1. The Embodiment of FIGS. 1-4

Figure 1:
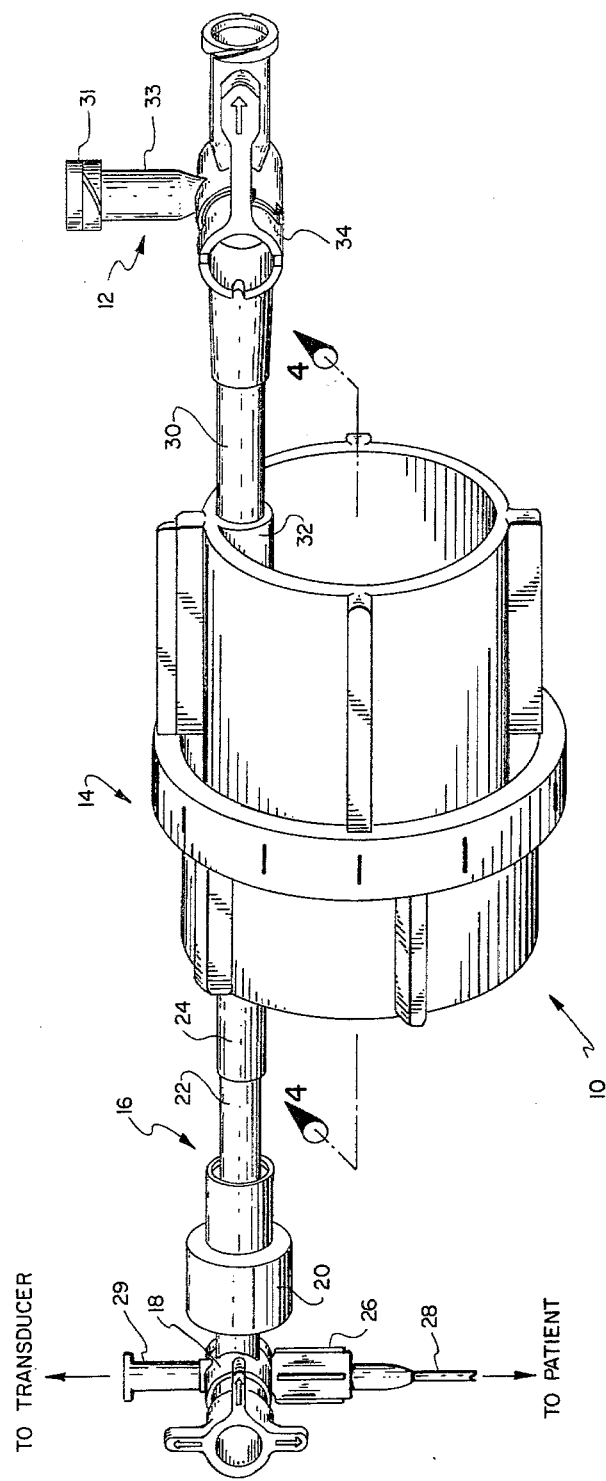
FIG. 1 is a perspective illustration of one presently preferred embodiment of the apparatus of the present invention, the apparatus being coupled in parallel to a liquid-filled catheter of a catheter-transducer system.

Referring to FIG. 1, one preferred embodiment of the apparatus of the present invention is generally designated at 10. The apparatus 10 generally consists of three components: a compliant air cavity generally designated 12; a variable impedance device generally designated 14; and fluid inlet member generally designated 16. Fluid inlet member 16 consists of a stopcock 18 coupled through a conventional luer fitting 20 to a short piece of plastic tubing 22. Tubing 22 is in turn attached to a coupling member 24 formed on the variable impedance device 14. Stopcock 18 is designed to be connected in parallel through a male coupling member 26 and tubing 28 to a catheter (not shown) that is inserted into a patient. The female coupling member 29 is attached to an electrical pressure transducer (not shown). As hereinafter more fully described, the catheter (not shown) and tubing 28 are filled with a liquid, typically a saline solution, so that hemodynamic pressures may be transmitted as pressure pulses through the liquid-filled catheter.

With further reference to FIG. 1, variable impedance device 14 is shown connected between the fluid inlet member 16 and the compliant air cavity 12. Compliant air cavity 12 consists of a female port 33 of stopcock 34 that is permanently capped by cap 31. Plastic tubing 30 is attached at one end to a coupling member 32 of the variable impedance device 14. The other end of tubing 30 is attached to stopcock 34. As hereinafter more fully described, stopcock 34 may be initially opened in order to fill the variable impedance device with liquid. Stopcock 34 may thereafter be closed so as to provide a compliant air cavity by virtue of the air entrapped in the female port 33 of stopcock 34.

Figure 2:
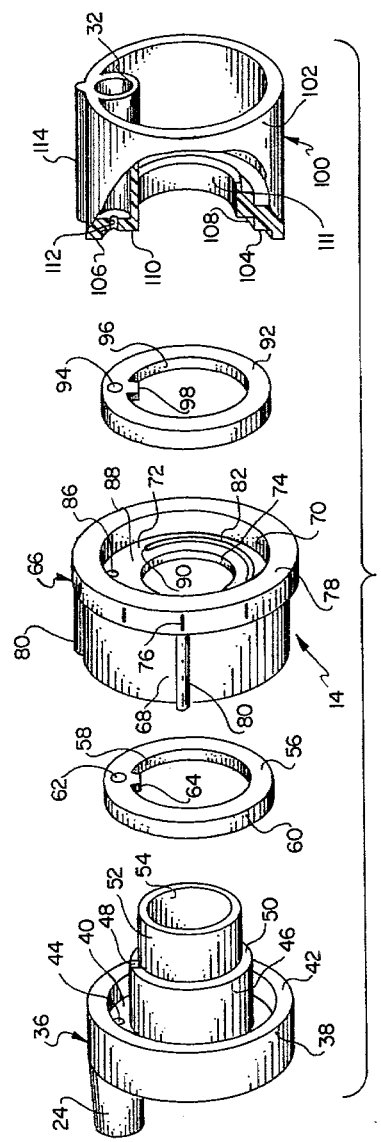
FIG. 2 is an exploded perspective illustration of the variable impedance device shown in FIG. 1.
Figure 4:
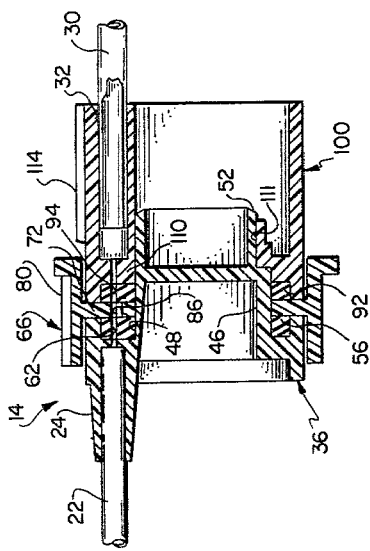
FIG. 4 is a cross-sectional view of the variable impedance device of FIG. 1 taken along cutting plane line 4-4.
Figure 3:
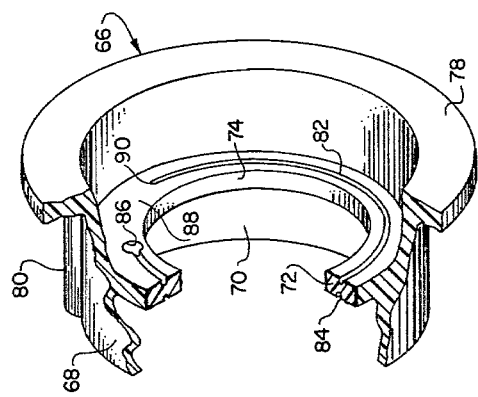
FIG. 3 is a fragmentary perspective illustration of the capillary disk of the variable impedance device of FIG. 2.

The variable impedance device 14 is best illustrated in FIGS. 2-4. The variable impedance device 14 has a cylindrical member 36 which is formed of a cylindrical body 38 which presents a coupling member 24. The coupling member 24 is eccentrically located adjacent the periphery of cylindrical body 38, and is attached to tubing 22 (see FIG. 1).

The body 38 circumscribes an annular disk 40 that is recessed away from the leading edge 42 of the body. The disk 40 is provided with a through-bore 44 that is disposed in alignment with the coupling member 24 and is in open communication therewith.

A bearing shaft 46 is formed integrally with the annular disk 40 and is centered with respect to the disk 40 and the body 38. The bearing shaft 46 has a longitudinal keyway 48 extending the entire length of the shaft 46 and opening at the leading end 50 thereof. The purpose for the keyway 48 will be described more fully hereafter. A diametrically reduced alignment shaft 52 is concentric with and extends axially from the bearing shaft 46. The alignment shaft 52 defines a space 54 which, for purposes of this illustration, is shown open.

An annular gasket 56 has a central opening 58 which is large enough to allow the gasket 56 to fit snugly over the bearing shaft 46. Preferably, when the gasket 56 is superimposed on the bearing shaft 46, the periphery 60 of the gasket 56 will fit snugly against the inside surface of the body 38. The transverse dimension of the gasket is selected so that the exposed face of the gasket 56 will project slightly beyond the face 42 of the body 38. The gasket 56 has a through-bore 62 which is similar in size to the through-bore 44 in disk 40. Alignment of the bores 62 and 44 is maintained by a key 64 projecting inwardly from the annular gasket 56. When the key 64 is situated within the keyway 48, alignment of the through-bores 62 and 44 is assured.

A sleeve generally designated 66 has a hub 68 which is cylindrical in configuration and has a smooth, hollow interior surface 70. A disk 72 is integrally formed on the interior surface 70 of the hub 68 and interiorly defines a diametrally reduced aperture 74. The sleeve 66 is shown in greater detail in FIG. 3. The disk 72 presents an open capillary 82 that is concentric with the disk 72 and is in the configuration of an open circle. The capillary 82, in the illustrated embodiment, is in the form of an open groove having a uniform cross-sectional area. The term capillary, as used herein, means an elongated passageway having a uniform cross-sectional area which hydraulically provides a resistance and an inertance which may be varied by controlling the effective length of the passageway.

Another capillary 84 precisely compliments the capillary 82 and is disposed on the face of the disk 72 opposite the face defining capillary 82. Capillary 82 and capillary 84 are joined at one end by a through-bore 86. Between the through-bore 86 and the terminal end 90 of the capillaries, the disk 72 presents a smooth portion 88.

The exterior of the hub 68 defines an annularly enlarged, radially projecting flange 78 at the leading end of the sleeve 66. Raised elements 80 may be formed on the exterior periphery of the hub 68 to facilitate gripping of the sleeve 66. Also, if desired, at least one of the raised elements 80 may be used to identify the location of the through-bore 86. Other markings, such as illustrated at 76, may be placed on flange 78 at locations corresponding to various changes in the effective length of capillaries 82 and 84.

As pointed out above, the disk 72 is spaced rearward of the flange 78 so as to be recessed within the hub 68. The aperture 74 defined by the disk 72 is adapted to be superimposed upon the bearing shaft 46 of the cylindrical body 38. It is observed that there is no key projecting into the opening 74 and, accordingly, the sleeve 66, even when superimposed upon the bearing shaft 46, is rotatable in relation thereto as will be subsequently more fully described.

A second gasket 92 which may be substantially identical to the gasket 56 is nested within the recess forward of the disk 72 and behind the flange 78. The gasket 92 has a through-bore 94 and defines a central aperture 96 adapted to be superimposed upon the bearing shaft 46. A key 98 projecting into the aperture 96 will maintain alignment of the through-bore 94 with the corresponding bores 62 and 44.

In the mentioned assembled relationship, as shown also in FIG. 4, the gaskets 56 and 92 serve to form a fluid seal with the capillaries 82 and 84, respectively. It will of course be recognized that the capillaries 82 and 84 may be located other than on the disk 72. Moreover, any suitable number of capillaries could be used to provide the necessary hydraulic impedance.

With further reference to FIG. 2, a cylindrical member 100 is adapted to nest within the hub 68 at the flange 78. Cylindrical member 100 has an elongated cylindrical body 102 which is preferably long enough in the axial dimension to allow the body 102 to be grasped easily with the fingers. As shown in the broken away portion, the body 102 has a diametrally reduced annular shoulder 104 which is sized so as to receive the gasket 92. Preferably, gasket 92 will project slightly beyond the trailing end 106 of the body 102 so that a fluid-tight seal will be formed between the cylindrical member 100 and the disk 72. An intermediate sleeve 108 is continuous with the shoulder 104 and sized so as to be superimposed upon the bearing shaft 46. A key 110 (shown best in FIG. 4) mates with the keyway 48 in the bearing shaft 46 so that the members 36 and 100 are nonrotatably connected one with the other.

The intermediate sleeve 108 is continuous with a diametrally reduced opening 111 which is adapted to snugly receive the alignment shaft 52 in press-fit relation. When the alignment shaft 52 is press-fit into the opening 111, adequate compressive force can be maintained on the gaskets 56 and 92 to assure a fluid seal in the entire variable impedance device 14.

The cylindrical member 100 also defines a coupling 32 as previously described that is attached to a short length of plastic tubing. The coupling 32 terminates in a diametrally reduced bore 112 that opens at the face 104 of cylindrical member 100. The bore 112 is disposed in alignment with the corresponding bores 94, 62 and 44 and is maintained in that alignment because of the locking relationship of the key 110 in keyway 48 (see FIG. 4).

In the use of the illustrated embodiment of the invention, the variable impedance device 14 is statically coupled in parallel to tubing 28 through tubing 22 and stopcock 18 (see FIG. 1). Variable impedance device 14 is also coupled at coupling 32 to a short length of plastic tubing 30 and stopcock 34. Stopcocks 34 and 18 are opened to permit fluid to enter the variable impedance device 14. Fluid will enter the variable impedance device 14 by way of tubing 22 and through-bores 44 and 62. Once fluid has entered the capillaries 82 and 84, through-bores 94 and 112 and tubing 30 and all air bubbles have been removed, stopcock 34 may be closed, providing a back pressure that prevents further escape of fluid from variable impedance device 14.

Disk 72 together with the capillaries 82 and 84 formed on the faces thereof may be rotated by grasping the hub 68 and rotating the hub about the axis of the bearing shaft 46. Depending upon the degree of rotation of the hub 68, the effective length of capillaries 82 and 84 may be varied in order to adjust the hydraulic impedance provided by capillaries 82 and 84.

The term impedance, as used herein, means a hydraulic resistance and/or a hydraulic reactance. The reactive component of the impedance may be derived either from a compliance or from an inertance. Inertance (sometimes called effective mass) is defined as fluid density times the effective length divided by the area of the hydraulic restriction.

The reactance due to a catheter-transducer system's compliance (i.e. the ability of the system to elastically yield in response to an applied force, such as an applied pulsation transmitted through the liquid-filled catheter), is a major factor in terms of causing unwanted resonance. Significantly, the parallel hydraulic impedance provided by the apparatus of the present invention can be used to somewhat offset the effect of a catheter-transducer system's compliance. Control of the parallel hydraulic impedance is advantageously achieved by the apparatus of the present invention by controlling the effective length of the capillaries 82 and 84, as described above. Thus, by rotating the disk 72 in the manner previously described, the effective length of capillaries 82 and 84 may be varied thus increasing or decreasing the parallel impedance to any desirable degree.

The compliant air cavity provided by the air filled female port 33 allows alternating pressure pulses to pass through the impedance provided by capillaries 82 and 84. Thus, the variable impedance device 14 operates in a static mode and serves to provide a variable impedance that may be adjusted over a wide range of values for purposes of accurately matching the characteristic impedance of an electromanometry system. Once the characteristic impedance of the electromanometry system is matched, unwanted resonance is significantly reduced, thus eliminating distortion and extending the range of frequencies over which the system may faithfully reproduce detected hemodynamic pressures.

2. The Embodiment of FIGS. 5–6

Figure 5:
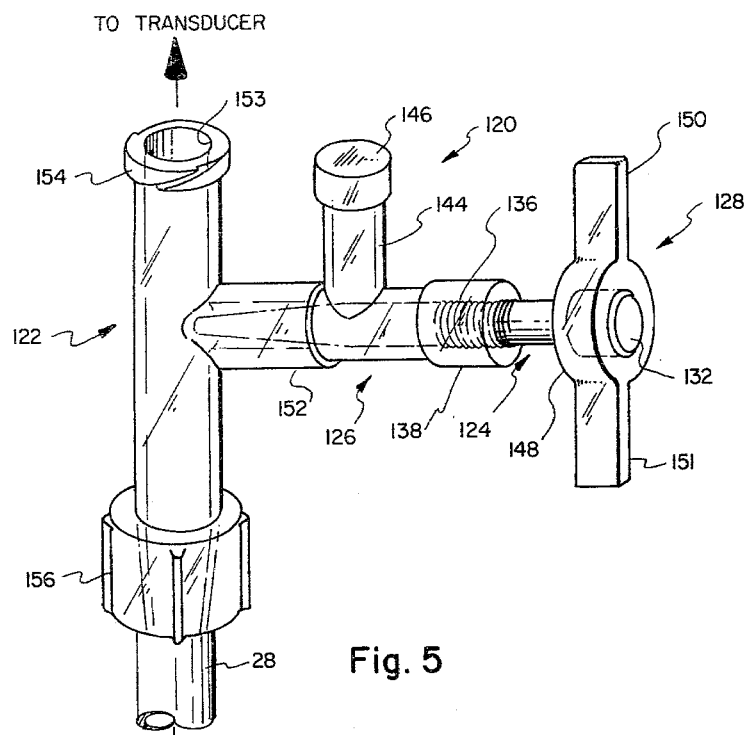
FIG. 5 is a perspective illustration of a second presently preferred embodiment of the present invention.
Figure 6:
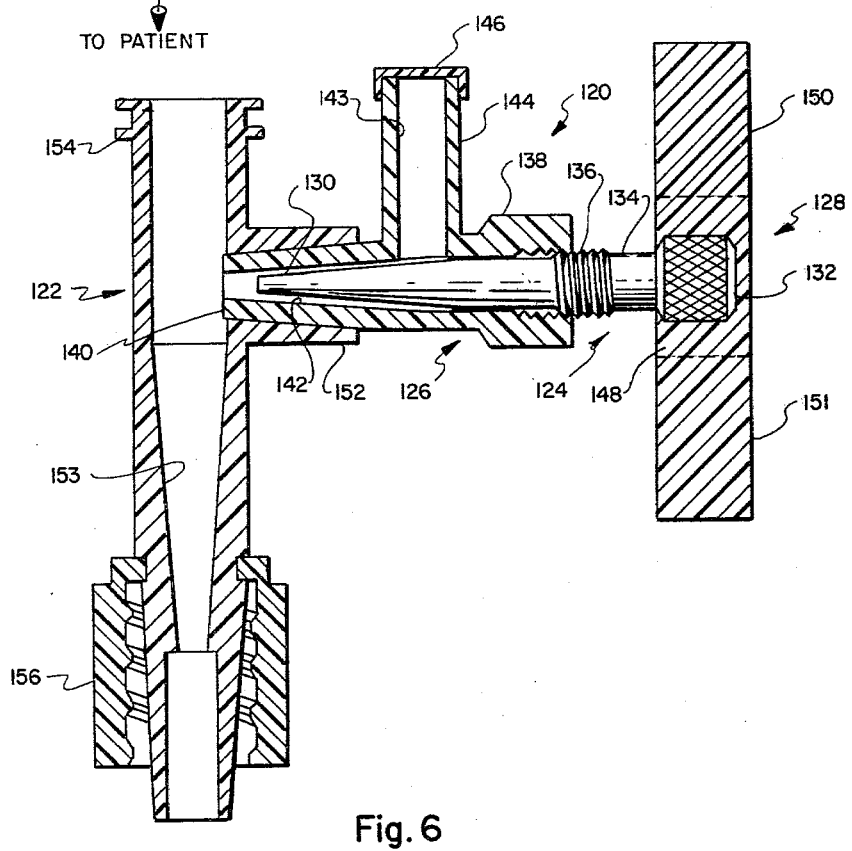
FIG. 6 is an enlarged cross-sectional view of the apparatus of FIG. 5.

A second preferred embodiment of the apparatus of the present invention is illustrated in FIGS. 5 and 6. As shown in FIGS. 5 and 6 the apparatus generally designated 120 consists of four components: a plastic T coupling member 122; a metal needle member 124; a unitary housing 126 molded around the tapered end and threaded middle portion of needle member 124; and a knob 128 molded onto the enlarged end of needle member 124.

As shown best in FIG. 6, the needle member 124 has a leading end 130 that is substantially elongated and tapered. The trailing end of needle member 124 terminates in an enlarged head 132. The surface of the enlarged head 132 is knurled to prevent slippage when the knob 128 is turned. Other suitable shapes for the enlarged head 132 could be used, as for example a hexagonal head.

Between the enlarged head 132 and tapered end 130 is a shaft 134 that is provided with a threaded portion 136. One end of housing 126 terminates in a collar 138 that is molded onto the threaded portion 136 of needle member 124. The other end of housing 126 terminates in an inlet port 140. The interior of inlet port 140 forms a tapered throughbore 142 that corresponds to the tapered end 130 of needle member 124. When needle member 124 is screwed all the way into housing 126 the leading tapered end 130 will protrude slightly beyond the end of the inlet port 140. Thereafter, as shown in FIG. 6 needle member 124 may be unscrewed so as to partially withdraw the tapered end 130 from the inlet port 140, resulting in a very small inlet channel formed between the interior throughbore 142 of inlet port 140 and tapered end 130 of needle member 124. As hereinafter more fully described, by positioning the tapered end 130 within inlet port 140 the area of the inlet channel may be varied so as to vary the impedance provided by the needle member 124 for purposes of matching the characteristic impedance of the electromanometry system.

Intermediate of the collar 138 and inlet port 140 of housing 126 there is a side port 144. The interior of side port 144 forms a chamber 143 that is in fluid communication with the inlet channel formed between inlet port 140 and tapered throughbore 142. The end of side port 144 is permanently capped with a cap 146. As hereinafter more fully described, the enclosed chamber 143 of side port 144 provides a compliant air cavity which is coupled through the variable impedance provided by the needle member 124.

With further reference to FIGS. 5 and 6 it will be seen that the knob 128 is molded directly onto the enlarged head 132 of needle member 124. Knob 128 has an enlarged, cylindrical base 148 which is joined to wings 150-151. The wings 150-151 provide increased leverage for purposes of screwing the needle member 124 into or out of the housing 126.

In the illustrated embodiment the needle member 124 is preferably fabricated from metal, such as stainless steel. Since the needle member 124 is constructed from metal, it will not melt when the housing 126 and knob 128 are insert molded around the needle member, as described below. It will of course be appreciated that certain types of high temperature plastics or ceramics could also be used to provide the needle member 124.

Housing 126 and knob 128 are preferably insert molded onto the needle member 124 so as to provide a precision seal about the leading tapered end 130 of the needle member 124. The type of plastic used for housing 126 and knob 128 may be any type of thermoplastic, as for example acrylic or styrene. By molding the housing 126 directly onto needle member 124 the inlet port 140 of housing 126 exactly fits the tapered end 130 of needle member 124. This advantageously eliminates any imprecision in the alignment between the tapered end 130 and the interior throughbore 142 of housing 140 which forms the inlet channel. Moreover, as the molten plastic cools during the molding process, it will shrink and create a hermetic seal around the tapered end 130 and threaded portion 136 of needle member 124. This eliminates the need for gaskets and eliminates the expense involved in terms of further assembly procedures that would otherwise be required to assemble the gaskets onto the needle member 124 to ensure a fluid-tight seal.

The T coupling 122 is also molded from plastic and is integrally attached to housing 126. T coupling 122 is attached to housing 126 at sleeve 152 which fits over the inlet port 140 and which is firmly welded or bonded thereto. One end of the coupling 122 terminates in a conventional female luer fitting 154 and the other end of the coupling member 122 terminates in a conventional male luer fitting 156. Like the embodiment previously described, female luer fitting 154 is adapted to be coupled to tubing (not shown) which leads to the electrical pressure transducer (not shown). The male luer fitting 156 is adapted to be coupled to the tubing 28 which leads to the catheter (not shown) that is inserted into the patient (not shown). The interior of coupling 122 forms a throughbore 153 through which the liquid-filled catheter (not shown) may be hydraulically coupled to the transducer (not shown).

In the use of the embodiment illustrated in FIGS. 5–6, the coupling member 122 is connected between the electrical pressure transducer (not shown) and the tubing 28 leading to the catheter that is inserted into the patient (not shown). The catheter-transducer system is then filled with a saline solution and the knob 128 of needle member 124 is then rotated so as to slightly withdraw the tapered end 130 of needle member 124 from the inlet port 140, as shown best in FIG. 6. As the knob 128 of needle member 124 is rotated, the small inlet channel formed by throughbore 142 (see FIG. 6) will permit entry of the fluid into the interior of side port 144. Only a limited amount of fluid will enter side port 144 because of the back pressure created by the enclosed end cap 146 on side port 144.

In the embodiment of FIGS. 5 and 6, the parallel impedance may be varied by controlling the area of the inlet channel formed by throughbore 142. Thus, by positioning the tapered end 130 of needle member 124 either further into or further out of the inlet port 140, the area of the restriction created by the needle member 124 may be increased or decreased thus varying the hydraulic impedance for purposes of matching the characteristic impedance of the electromanometry system.

The compliant air cavity provided by the enclosed side port 144 allows alternating pressure pulses to pass through the impedance provided by needle member 124. Thus, like the prior embodiment, the embodiment of FIGS. 5–6 operates in a static mode and serves to provide a hydraulic impedance that may be adjusted over a wide range of values for purposes of accurately matching the characteristic impedance of virtually any type of electromanometry system. Once the characteristic impedance of the electromanometry system is matched, unwanted resonance is significantly reduced thus eliminating distortion and extending the range of frequencies over which the system may faithfully reproduce detected hemodynamic pressures.

The invention may be embodied in other specific forms without departing from its spirit or essential characteristics. The described embodiment is to be considered in all respects only as illustrative and not restrictive and the scope of the invention is, therefor, indicated by the appended claims rather than by the foregoing description. All changes which come within the meaning and range of equivalency of the claims are to be embraced within their scope.

What is claimed and desired to be secured by United States Letters Patent is:

1. In an electromanometry system having a liquid-filled catheter coupled to an electrical pressure transducer for monitoring hemodynamic pressures, a variable restriction apparatus comprising a valve for hydraulically matching the characteristic impedance of the electromanometry system for purposes of controlling the system's resonance characteristics and thereby improving the system's frequency response, said valve comprising:

a needle member having a first elongated end that is tapered and a second end, with a threaded portion intermediate said first and second ends; and a housing, said housing comprising a first port in fluid communication with said liquid-filled catheter, said first port being molded onto at least a portion of said tapered end, a collar molded onto the threaded portion of said needle member, and a second port in fluid communication with said first port, said second port being molded so that it is adjacent to at least a portion of said tapered end and being capped so as to provide a compliant air cavity.

2. The apparatus of claim 1 further comprising a knob member affixed to said second end of the needle member to facilitate rotation thereof, whereby the hydraulic impedance may be varied by adjusting the position of said first tapered end of the needle member relative to said first port that is molded thereon.

3. In an electromanometry system having a liquid-filled catheter and means for providing a variable hydraulic restriction connected in parallel to said liquid-filled catheter, said means for providing a variable hydraulic restriction comprising a valve which comprises a needle member having a first elongated end that is tapered and a second end configured as a knob member, with a threaded portion intermediate said first and second ends, and which further comprises a housing molded onto a portion of said needle member, said housing having an inlet port in fluid communication with said liquid-filled catheter, said inlet port being sealed around at least a portion of said tapered end, a collar molded onto the threaded portion of said needle member, and a side port in fluid communication with said inlet port, said side port being molded so that it is adjacent to at least a portion of said tapered end and being capped at the open end thereof so as to form a compliant air cavity therein, a method of matching the characteristic impedance of the electromanometry system for purposes of controlling the system's frequency response, said method comprising the step of rotating said knob member so as to adjust the position of the tapered end of said needle member within said first port, thereby adjusting the parallel hydraulic restriction provided by the tapered end of said needle member so that the characteristic impedance of the electromanometry system will be matched by the impedance of said restriction and compliant cavity.

* * * * *